United States Patent [19]

Uylen et al.

[11] Patent Number: 5,474,902
[45] Date of Patent: Dec. 12, 1995

[54] SEMI-PERMEABLE CAPILLARY ASSAY DEVICE

[75] Inventors: Marcelus H. F. Uylen, Berghem; Leonardus P. C. Kuijpers, Boxtel, both of Germany

[73] Assignee: Akzo Nobel N.V., Arnhem, Netherlands

[21] Appl. No.: 190,699

[22] Filed: Feb. 2, 1994

Related U.S. Application Data

[63] Continuation of Ser. No. 772,768, Oct. 7, 1991, abandoned.

[30] Foreign Application Priority Data

Oct. 8, 1990 [EP] European Pat. Off. ............ 90202666

[51] Int. Cl.$^6$ .................... G01N 33/543; G01N 33/546; G01N 33/553
[52] U.S. Cl. ................ 435/7.9; 422/56; 422/57; 422/58; 422/101; 435/7.92; 435/7.93; 435/7.94; 435/810; 435/975; 436/164; 436/514; 436/518; 436/524; 436/525; 436/528; 436/531; 436/533; 436/534; 436/536; 436/541; 436/805; 436/808; 436/810
[58] Field of Search ................ 422/55–59, 99–102; 435/810, 970, 975, 7.9, 7.92, 7.93, 7.94; 436/518, 541, 164, 165, 805, 808, 810, 514, 536, 524, 525, 528, 531, 533, 534

[56] References Cited

U.S. PATENT DOCUMENTS

| 4,920,046 | 4/1990 | McFarland et al. ................... 436/518 |
| 4,943,522 | 7/1990 | Eisinger et al. ......................... 435/810 |

FOREIGN PATENT DOCUMENTS

| 0349215 | 1/1990 | European Pat. Off. . |
| 2204398 | 11/1988 | United Kingdom ................... 435/970 |
| WO8806650 | 5/1988 | WIPO . |

*Primary Examiner*—David Saunders
*Assistant Examiner*—Christopher L. Chin
*Attorney, Agent, or Firm*—William M. Blackstone; Gregory R. Muir; Mary E. Gormley

[57] ABSTRACT

A method and a device for performing an assay in order to detect or determine the amount of an analyte in a test liquid, wherein bound and unbound reactants can be separated, comprising a capillary canal for liquid transport that is at least partly bordered by a semi-permeable layer, wherein during performance of an assay a movable solid phase material bearing a ligand capable of binding the analyte or binding a reactant for the analyte is within the capillary channel adjacent to the semi-permeable layer, said semi-permeable layer having pores that are sufficiently small to prevent the passage of the movable solid phase material and sufficiently large to permit passage of unbound reactants there through.

18 Claims, 1 Drawing Sheet

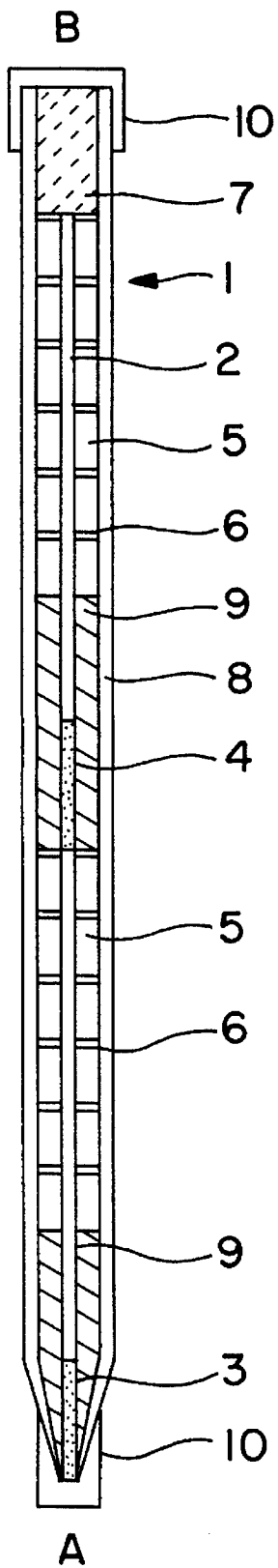
FIG. I

SEMI-PERMEABLE CAPILLARY ASSAY DEVICE

This is a continuation of application Ser. No. 07/772,768, filed Oct. 7, 1991, now abandoned.

The invention relates to a device and the use of the device for detecting and/or determining an analyte in a test liquid and a method for detecting and/or determining an analyte in said test liquid.

BACKGROUND OF THE INVENTION

The field of specific binding assays has greatly expanded as its importance in the diagnostic field has become recognized. The ability to detect a specific compound and measure the compound quantitatively has permitted the monitoring of the administration of a wide variety of drugs, the determination of an imbalance in a wide variety of hormones, the quantitation of physiologically active proteins and the diagnosis of the presence of a pathogen. Different techniques have been distinguished in requiring or not requiring separation steps, the nature of the signal developed by the label, the development of the signal in a solution or on a surface and the manner of measurement for quantitative determination.

In developing an assay, there are a number of considerations in devising the reagents and protocol. One consideration is the degree of sophistication of the individual performing the assay. There are a lot of situations where it is desirable that a relatively untrained or unexperienced individual should be able to perform an assay and obtain reasonably quantitative results. It is particularly desirable that the untrained person be able to perform a quantitative assay with a rapid simple test without the need for sophisticated instruments.

In the last decade an enormous amount of so-called dipsticks and filter assays have been developed varying from all kinds of paper strips in different shapes, promising a better result than a previous strip, to plastic strips, coated with, for instance, an immunochemical component.

For instance, European patent application EP 0,149,168 describes an immunoassay which can be carried out by making use of a capillary glass tube. At least 2 regions are packed with separate carrier material. An immunoreactive component provided with a labelling substance which, via an immunochemical reaction, is capable of forming an immunocomplex with a substance, whose presence or concentration in the test liquid is desired to determine, is bound to the first carrier material. Subsequently, said complex is transported by capillary action and ends up in the second carrier material where it is immobilized after binding to a second immunoreactive component which is bound to the second carrier material. Thereafter the quantity of immunocomplex, thus immobilized, can be measured via known detection methods depending on the labelling substance used. The labelling substances used in the European application in question are radioisotopes, enzymes or fluorescent substances.

A disadvantage of said immunoassays is that after the immunochemical reaction, several operations always have to be performed to separate bound solid phase from non-reacted reactants, which action is known to those skilled in the art as "bound/free separation". Additional operation steps are needed to add reagents after bound/free separation, which is for instance the case when a substance has to be added to detect a solid phase bound labelled reactant. An additional step is needed for certain when applying highly sensitive assays requiring enhancement of the assay signal.

Surprisingly, a device has now been found with which the operations to be performed remain confined to bringing a device into contact with a test liquid and a wash fluid and determining the result—after some time—without impairing the accuracy and reliability, making it possible also to perform complex assays, e.g. ELISA, with only two operation steps, irrespective the number of bound/free separations and reagent additions and the sequence thereof.

BRIEF SUMMARY OF THE INVENTION

The invention therefore relates to a device for performing an assay in order to detect and/or determine an analyte in a test fluid, said device comprising a track for liquid transport, at least partly bordered by a semi-permeable layer, in said track is transported during the assay and alongside the semi-permeable layer a movable solid phase material bearing a ligand capable to bind, directly or indirectly, the analyte and/or to bind, directly or indirectly, a reactant for the analyte, said semi-permeable layer being incapable to let pass the movable solid phase material.

The invention also relates to a method for detecting and/or determining an analyte in a test liquid by bringing the device according to the invention into contact with said liquid and, when appropriate, with a transporting liquid so that the movable solid phase material provided with a ligand comes into contact with said test liquid and, simultaneously or subsequently, with a reactant provided with a label and is transported by one or both of said liquids through the track to a position in the device where a detecting system for the label is located and the label being bound, directly or indirectly, to said solid phase material is detected, in that the degree of binding is determined directly or indirectly, which degree is a qualitative or quantitative indication of the concentration of the analyte to be determined or detected.

The invention also relates to a test kit which may include a device according to the invention. Optionally the test kit may contain, in or outside the device, an immunochemical reagent coupled to a label and a movable dispersed or dispersable solid phase material bearing a ligand e.g. an immunochemical reagent. In another performance the test kit may contain, in or outside the device, a nucleic acid sequence coupled to a label and a movable, dispersed or dispersable solid phase material bearing a ligand e.g. a nucleic acid sequence.

The track in the device according to the invention may contain provisions to control the velocity of the liquid flux in said track. Such provisions may be components which slowly dissolve upon wetting e.g. like sucrose.

BRIEF DESCRIPTION OF THE FIGURE

FIG. 1 is a drawing of one embodiment of the device.

DETAILED DESCRIPTION OF THE INVENTION

A particular embodiment of the device is a device in which the track is a capillary canal e.g. a porous hollow fibre of e.g. polyethersulfone, polyamide, polyimide or regenerated cellulose, containing walls that are semi-permeable and that is at least partly surrounded by absorbent material and in which this canal is used to forward, by capillary force, the movable solid phase material e.g. a watery suspension of particles coated with a ligand. The semi-permeable wall is capable of letting molecules pass, molecules e.g. contaminations or particles smaller than said coated particles, e.g. molecules, through its pores, however not the said coated particles.

The pores may be present in the semi-permeable wall in e.g. a tortuous, parallel or at an approximate perpendicular orientation.

The capillary canal may end in, or depart from, stations containing reagents, which reagents may be said suspension, labelled or non-labelled specific reactants or a specific substrate to detect the labelled reactant.

The capillary canal may contain such stations itself. Said semi-permeable wall may be in contact with reagents outside the capillary canal. Reagents outside the canal may penetrate the canal across the semi-permeable wall e.g. upon wetting. Reagents may be dry reagents, which dissolve or resuspend upon contact with the test liquid or a transporting fluid that is transported through the canal.

For the benefit of bound/free separation the semi-permeable wall of the capillary canal may be in contact with an absorbent for liquid outside the capillary canal.

However, the semi-permeable wall itself may have a sufficient absorbing capacity to make an absorbent redundant.

Bundles of capillary canals rather than a single capillary canal may be used.

Another embodiment according to the invention can be constructed and function analogously to the above-mentioned device by using a porous matrix, rather than a capillary canal, provided this matrix is capable of transporting said coated particles and that this matrix is, at least partly, alongside in contact with said semi-permeable layer. The device according to the invention may be used for bound/free separation in immunological, nucleic acid hybridization or nucleic acid amplification assay systems.

A particular device is described with reference to FIG. 1. The device (1) (see FIG. 1) consists of a tubular semi-permeable membrane e.g. a porous hollow fibre (2) filled with dry dispersable movable solid phase material e.g. lyophylized polystyrene latex particles (3) coated with ligand for the analyte. Further upstream the fibre capillary has been filled with a dry, e.g. lyophilized, labelled reactant (4) for the analyte. The porous hollow fibre is at least partly surrounded by absorbent material (5), separated by polymer layers (6) which do not let pass watery liquids.

Depending on the label used, dry substrate (7) reactive for the label is located at the end of the device. The detection and/or determination of the assay performed takes place at said end of the device.

Optionally the porous hollow fibre, surrounded with absorbent material, has been provided with a casing (8) such as an oval or round tube, or a square or rectangular casing, which casing at the casing open ends A and B may be closed with a cap (10).

The casing is, at least at the position of the determination or detection place, manufactured from transparent material. Suitable materials for a casing and the caps are glass or plastics, such as polystyrene, polypropylene, nylon, polycarbonate or polyvinylchloride.

Rather than using polystyrene latex particles (3), as a movable solid phase material, any particle capable to be transported by a liquid flux and to be coated with a ligand can be used as long as these particles can exist as a dispersion in said liquid and provided these particles are incapable of passing the semi-permeable membrane. Said movable solid phase material according to the invention is a dispersed or dispersable solid phase material; the dispersable solid phase material becoming dispersed upon contact with a liquid. Said particles may be micro-crystalline cellulose, polyacrylamide spheres, stabilized blood cells, blood cells from the sample itself, metal sols etc. Such particles may also be coloured as a built-in visible proper control on the transport of the movable solid phase material e.g. to observe arrival at the site where the substrate is present (7) in order to be sure that the test is completed.

In the embodiment of FIG. 1 e.g. latex particles may be coloured to observe arrival of the movable solid phase material at the site where the substrate is present (7). Said ligands, either antigens or fragments thereof, antibodies or fragments thereof or nucleic acid sequences can be coated to the particles either by physical adsorption or chemical binding e.g. covalent binding.

The lyophilized labelled reactant (4) can be labelled antigens or fragments thereof, antibodies or fragments thereof or nucleic acid sequences. These reactants can be located in or outside the capillary canal. Reactants outside the canal are localized that way that these reactants dissolve upon wetting and enter the canal across said semi-permeable membrane.

The term "label" should be understood to mean an enzyme, a dyestuff sol particle, a metal sol particle or other coloured disperse particles as long as above-mentioned labelled reactant is capable of passing through the pores of the semi-permeable membrane.

The dyestuff sol particle, the metal sol particle or other coloured disperse particles function as a directly detectable labelling substance. When an enzyme has been chosen as a label, a dry substrate (7) reactive for the enzyme is present at the detection or determination site at the end of the device. Rather than or in addition to a substrate an electronical sensor, directly or indirectly, sensitive for the presence of the label, may be present.

In case one uses a metal sol particle as a labelling substance it is possible to fill the end of the device (7) with for instance an intensifying substance for said metal sol capable to enhance the sensitivity of the result, yielding a signal visible by eye or readable colourimetrically or reflectometrically.

Methods for coupling said labels to immunochemically active substances are known per se and do not form part of the present invention. The coupling may be direct or indirect, chemical, e.g. covalently, and non-chemical, e.g. adsorptively.

The enzyme Horse Radish Peroxidase (HRP) is often used as a suitable label. Substrate for this HRP is hydrogen peroxide, which has to be mixed with a chromogenic co-substrate e.g. 3,3',5,5'-tetramethylbenzidine (TMB).

Absorbent material (5) may be composed of materials such as cellulose, cotton, wool, silk, glass fibres, nylon fibres, acrylic fibres, polyethylene fibres, polyester fibres or ceramics or hardening materials such as gypsum. Absorbent materials may be composed of powders or granulates, such as chalk, norit or silicagel.

Optionally the absorbent material may contain active, e.g. immunochemically active, substances with affinity for contaminating components in the test liquid.

Using the device according to the invention various kind of analytes can be determined with said device: antigens or fragments thereof, antibodies or fragments thereof and haptens as well as nucleic acid sequences.

The device is of use in determining analytes in test liquids, such as urine, serum or whole blood. The device is suitable for performing a so-called sandwich reaction, an inhibition or competition or blocking reaction.

The use of a prefered embodiment of the device according to the invention for performing an immunoassay detecting an immunochemically active substance in a test liquid will be explained in more detail.

The device according to the invention is brought into contact with a test liquid by placing one end of its capillary canal in a test liquid, or by dipping this end in a test liquid and subsequently placing it in a transporting liquid. By this an assay e.g. ELISA (enzyme linked immuno sorbent assay) is performed autonomously. A typical assay mechanism is:

the liquid resuspends the movable solid phase material e.g. lyophilized particles coated with ligand, the test liquid and/or a transporting liquid forward(s) the movable solid phase material through the capillary canal, either simultaneously or subsequently said liquid enables a labelled reactant to come into contact with said coated particles, as a consequence of this the labelled reactant binds to the particles in case the analyte being present in the test liquid, unbound substances, like unbound analyte, unbound labelled reactant and contaminants, are removed from the canal and thus separated from the particles by a liquid stream through the semi-permeable membrane, which hereto is in contact with absorptive matter outside the canal, upon further transport through the capillary, the liquid transporting the particles dissolves, in case of an ELISA, the components of a substrate, as a consequence of which this substrate comes into contact with the particles, label, bound onto this particles, converts the substrate to yield a reaction product that is visible by eye or that can be measured colourimetrically or by reflectometry.

Said typical assay mechanism may function analogously with a metal sol or dye stuff sol as a label instead of an enzyme as a label. When using a metal sol or dye stuff sol as a label, a substrate may be superfluous.

The device has enormous advantages as compared with conventional dipsticks and filter assays. The disperse solid phase material, e.g. latex particles coated with antibodies, remains in suspension so that always an optimal interaction between the reaction components is obtained and by this a higher sensitivity is obtained and/or shorter incubation time is achieved.

Using conventional solid phase filter techniques non-specific interactions occur with the solid phase filter material. Using the device according to the invention, contaminating components interactive with the semi-permeable membrane are not able to interfere with the eventual detection process.

The device can be used as an easy manual, rapid assay for all kinds of liquid biological samples of human or animal origin. The samples can be body fluids, excrements, tissue preparations, saliva etc. or liquid extracts thereof.

The invention is explained with reference to the following examples.

EXAMPLE I

Onto the surface of 800 nm polystyrene latex particles anti-HBs (antibodies against hepatitis B surface antigen (HBsAG)) was coupled through physical adsorption according to the method as described by Fritz and Rivers (1972 J. Immunology 108, 108–111). HRP was conjugated to anti-HBs according to Wilson and Nakane (1978). A 10 cm piece of a polyamide porous hollow fibre (PHF), with an inner diameter of 310 µm and composed of a 75 µm thick tubular polyamide membrane with 200 up to 500 nm pores was filled at one end (A) over a length of 1 cm with a suspension of the above produced anti-HBs loaded latex particles and approximately 5 up to 6 cm from the end (A) the capillary was filled over a length of approx 1 cm with the anti-HBs/ HRP conjugate. This was achieved by cutting the 10 cm piece in two halves, filling one end of each half over a length of 1 cm with liquid reagents, by subsequent lyophilization of the fibres containing the liquid reagents and by coupling the two halves by means of a socket.

To construct a test device for HBsAg, said fibre was subsequently brought into approximately the centre of a tubular transparent holder with an inner diameter of 0.5 cm and a length of approx. 11 cm. At one end, corresponding with the end A of the hollow fibre, the tubular holder was conical over a length of 1 cm and had a hole through which the hollow fibre ends. The space around the fibre in the plastic holder was filled with layers of powdered cellulose, separated by thin polymer layers which do not let pass watery liquids according to the below scheme (number between dashes refer to FIG. 1):

| Subsequent materials inside the capillary starting from lower end A | Subsequent materials inside the holder around the capillary starting at lower end A |
| --- | --- |
| 1 cm lyophilized latex (3) 4 cm empty | 2,0 cm polymer (9) 6 × 0,45 cm powdered cellulose (5) 0,05 cm polymer (6) |
| 1 cm lyophilized conjugate (4) 4 cm empty | 2,0 cm polymer (9) 6 × 0,45 cm powdered cellulose (5) 0,05 cm polymer (6) inside the holder on top of the capillary near end B: 1 cm substrate station (7) |

The substrate station was constructed by impregnating a piece of ceramics with a mixture of hydrogen peroxide and TMB in an appropriate buffer system and by subsequent drying the piece under vacuum at 18°–25° C.

At the end (B), opposite to the end (A), the open end of the fibre is covered with this substrate station. The ceramics allow the latex spheres to pass. On the end (A) and on the end (B) the device was closed with a plastic cap (10).

Tests, with a total test duration of 10 minutes, were performed using devices constructed as above. Caps (10) were removed from the device. In an approximately vertical position the device was dipped with the end A in a serum sample for 30 seconds, which allowed the sample to penetrate into the canal over a length of approx 2 cm. Subsequently the device was placed at the end A in demineralized water at an angle of 15 degrees (deviating from horizontal) and kept so for 10 minutes. Subsequently the colour produced in the substrate station was read by eye. A dilution series of HBsAg in serum was tested with the above device.
Results as produced by the device:

| HBsAg dilution series | Read by eye |
| --- | --- |
| 1000 ng/ml: | strong blue colour |
| 100 ng/ml: | strong blue colour |
| 10 ng/ml: | blue colour |
| 0 ng/ml: | no blue colour |

This proves the system is valid as a rapid single manual assay for HBsAg.

EXAMPLE II

Analogously to the methods as described in Example I, anti-hCG (antibody against human chorion gonadotrophin (hCG)) was coupled to 800 nm latex particles and HRP was conjugated to anti-βhCG (antibody that reacts with an epitope located on the β subunit of hCG). Devices were constructed as described in Example I, implementing the above hCG specific reagents instead of the HBsAg specific reagents.

A dilution series of hCG was made, using a diluent consisting of a mixture of urine specimen of fertile non-pregnant women. This dilution series was tested analogously to the procedure for testing as described in Example I, using the above mentioned devices.

Results as produced by the device:

| hCG dilution in urine series | Read by eye |
| --- | --- |
| 2500 U/l | strong blue colour |
| 250 U/l | strong blue colour |
| 25 U/l | blue colour |
| 0 U/l | no blue colour |

This demonstrates that the device can be used to perform a rapid single manual assay for the detection of hCG in urine samples and is consequently very suitable for pregnancy testing.

We claim:

1. A device for performing an assay in order to detect or determine the amount of an analyte in a test liquid, wherein bound and unbound reactants can be separated, comprising:

a casing with a test liquid entry point where test fluid enters the device;

a capillary canal held within said casing and in fluid communication with said test liquid entry point for liquid transport, said capillary canal at least partly bordered by a semi-permeable layer, wherein during performance of an assay a movable solid phase material bearing a ligand which, directly or indirectly, binds to the analyte or a labeled reactant that is specific for the analyte or competitively binds with the analyte is within the capillary canal, said semi-permeable layer having pores that are sufficiently small to prevent passage of the movable solid phase material but sufficiently large to permit passage of unbound labeled reactant and unbound analyte there through; and a detection area in said casing downstream of said capillary canal with means for detection of labeled reactant bound to the movable solid phase material.

2. The device according to claim 1, wherein said capillary canal is a porous hollow fibre.

3. The device according to claim 1, wherein said semi-permeable layer is in contact with an absorbent and said semi-permeable layer is located between said capillary canal and said absorbent.

4. The device of claim 3, wherein the absorbent material is comprised of a plurality of absorbent material layers separated from each other by polymer layers that do not let watery liquids pass.

5. The device according to claim 1, wherein either or both the ligand and the labeled reactant specific for the analyte are immunochemical reagents.

6. The device according to claim 5, wherein the reactant is an enzyme-labeled reactant.

7. The device according to claim 5, wherein the labeled reactant is a metal sol particle coated with an immunochemical reagent.

8. The device according to claim 1, wherein the movable solid phase material comprises polymer particles.

9. A device according to claim 1, wherein the semi-permeable layer has liquid absorbent capacity.

10. The device of claim 1, wherein the capillary canal contains the labeled reactant.

11. The device of claim 1, wherein the capillary canal contains the moveable solid phase material.

12. The device of claim 11, wherein the capillary canal contains said labeled reactant.

13. A method for detecting or determining the amount of an analyte in a test liquid comprising:

a) contacting the device according to claim 12 with said test liquid, thereby b) contacting said liquid with the movable solid phase material coated with a ligand which, directly or indirectly, binds to the analyte or a labeled reactant that is specific for the analyte or competitively binds with the analyte to form a mixture, c) contacting, either simultaneously or subsequently, the mixture of step b) with said labeled reactant, d) transporting the resulting mixture of step c) through said device such that the movable solid phase material is transported to the detection area, and e) detected labeled reactant bound to said movable solid phase material to qualitatively or quantitatively determine the presence or concentration of said analyte.

14. A method for detecting or determining the amount of an analyte in a test liquid comprising:

a) forming a mixture by contacting said test liquid with a movable solid phase material coated with a ligand which, directly or indirectly, binds to the analyte or a labeled reactant that is specific for the analyte or competitively binds with the analyte, b) contacting, either simultaneously or subsequently, the mixture of step a) with said labeled reactant, c) contacting the device according to claim 1 with the resulting mixture of step b), thereby d) transporting the resulting mixture of step b) through said device such that the movable solid phase material is transported to the detection area, and e) detecting labeled reactant bound to said movable solid phase material to qualitatively or quantitatively determine the presence or concentration of said analyte.

15. A test kit for performing an immunoassay to detect or determine the amount of an analyte in a test sample comprising:

the device of claim 1;

a movable, dispersable solid phase material bearing a ligand which, directly or indirectly, binds to the analyte or a labeled reactant that is specific for the analyte or competitively binds with the analyte; and a labeled reactant that is specific for the analyte or competes with the analyte.

16. The test kit of claim 15, wherein the solid phase material bearing the ligand is disposed within the capillary canal of the device.

17. The test kit of claim 16, wherein the device further comprises the labeled reactant disposed within the capillary canal.

18. The test kit of claim 15, wherein the labeled reactant is disposed within the capillary canal.

* * * * *

UNITED STATES PATENT AND TRADEMARK OFFICE
CERTIFICATE OF CORRECTION

PATENT NO. : 5,474,902
DATED : December 12, 1995
INVENTOR(S) : Marcelus H.F. Uylen and Leonardus P.C. Kuijpers It is certified that error appears in the above-indentified patent and that said Letters Patent is hereby corrected as shown below:

Please correct the Inventors section on the title page, line 3, by deleting "Germany" and inserting --    Netherlands -- therefor.

Signed and Sealed this

Twenty-first Day of May, 1996

Attest:

BRUCE LEHMAN

Attesting Officer           Commissioner of Patents and Trademarks